(12) United States Patent
Seki (10) Patent No.: US 10,485,794 B2
(45) Date of Patent: Nov. 26, 2019

(54) TREATMENT METHOD BY COMBINED USE OF MDM2 INHIBITOR AND BTK INHIBITOR

(71) Applicant: DAIICHI SANKYO COMPANY, LIMITED, Tokyo (JP)

(72) Inventor: Takahiko Seki, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/566,336

(22) PCT Filed: Apr. 12, 2016

(86) PCT No.: PCT/JP2016/061762
§ 371 (c)(1),
(2) Date: Oct. 13, 2017

(87) PCT Pub. No.: WO2016/167236
PCT Pub. Date: Oct. 20, 2016

(65) Prior Publication Data
US 2018/0117025 A1 May 3, 2018
US 2018/0353493 A9 Dec. 13, 2018

(30) Foreign Application Priority Data

Apr. 13, 2015 (JP) .................. 2015-082013

(51) Int. Cl.
A61K 31/4439 (2006.01)
A61K 31/519 (2006.01)
A61P 35/02 (2006.01)

(52) U.S. Cl.
CPC ........ *A61K 31/4439* (2013.01); *A61K 31/519* (2013.01); *A61P 35/02* (2018.01); *A61K 2300/00* (2013.01); *Y02A 50/385* (2018.01)

(58) Field of Classification Search
None
See application file for complete search history.

(56) References Cited

U.S. PATENT DOCUMENTS

| | | | | |
|---|---|---|---|---|
| 2012/0264738 A1* | 10/2012 | Sugimoto | ............ | C07D 487/10 514/210.21 |
| 2013/0165424 A9 | 6/2013 | Sugimoto et al. | | |

FOREIGN PATENT DOCUMENTS

| | | |
|---|---|---|
| CA | 2884238 A1 | 3/2014 |
| WO | WO 2004/096134 A2 | 11/2004 |
| WO | WO 2006/024837 A1 | 3/2006 |
| WO | WO 2006/091646 A2 | 8/2006 |
| WO | WO 2006/136606 A2 | 12/2006 |
| WO | WO 2007/104664 A1 | 9/2007 |
| WO | WO 2007/104714 A1 | 9/2007 |
| WO | WO 2008/034736 A2 | 3/2008 |
| WO | WO 2008/036168 A2 | 3/2008 |
| WO | WO 2008/039218 A2 | 4/2008 |
| WO | WO-2008039218 A2 * | 4/2008 ............ A61K 31/00 |
| WO | WO 2008/055812 A1 | 5/2008 |
| WO | WO 2008/119741 A2 | 10/2008 |
| WO | WO 2008/141917 A1 | 11/2008 |
| WO | WO 2008/141975 A1 | 11/2008 |
| WO | WO 2009/077357 A1 | 6/2009 |
| WO | WO 2009/080488 A1 | 7/2009 |
| WO | WO 2010/009342 A2 | 1/2010 |
| WO | WO 2010/028862 A1 | 3/2010 |
| WO | WO 2010/031713 A1 | 3/2010 |
| WO | WO 2010/084097 A1 | 7/2010 |
| WO | WO 2010/091979 A1 | 8/2010 |
| WO | WO 2010/094622 A1 | 8/2010 |
| WO | WO 2010/121995 A1 | 10/2010 |
| WO | WO 2011/153514 A2 | 12/2011 |
| WO | WO 2012/121361 A1 | 9/2012 |
| WO | WO 2013/059738 A2 | 4/2013 |
| WO | WO 2013/155347 A1 | 10/2013 |
| WO | WO 2014/071109 A1 | 5/2014 |
| WO | WO 2014/071231 A1 | 5/2014 |
| WO | WO 2014/143807 A2 | 9/2014 |
| WO | WO 2014/159745 A1 | 10/2014 |
| WO | WO 2014/168975 A1 | 10/2014 |
| WO | WO 2014/194254 A1 | 12/2014 |
| WO | WO 2015/015013 A1 | 2/2015 |
| WO | WO 2015/017812 A1 | 2/2015 |
| WO | WO 2017/069289 A1 | 4/2017 |

OTHER PUBLICATIONS

Saiki et al. "MDM2 antagonists synergize broadly and robustly with compounds targeting fundamental oncogenic signaling pathways" Oncotarget, vol. 5, No. 8 pp. 2030 (Year: 2012).*

Lesley et al. "High-throughput combinatorial screening identifies drugs that cooperate with ibrutinib to kill activated B-cell-like diffuse large B-cell lymphoma cells," PNAS Feb. 11, 2014; vol. 111; No. 6 pp. 2349-2354. (Year: 2014).*

Cameron et al., "Ibrutinib: First Global Approval," *Drugs*, (2014), 74:263-271.

(Continued)

*Primary Examiner* — Jeffrey S Lundgren
*Assistant Examiner* — Michael J Schmitt
(74) *Attorney, Agent, or Firm* — Dorsey & Whitney LLP (57) ABSTRACT

It is intended to provide a medicament and a method for treating cancer comprising a compound having MDM2 inhibiting activity and a compound having BTK inhibiting activity in combination. The present invention provides a medicament comprising (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydro-dispiro[cyclohexane-1,2'-pyrrolidine-3',3"-indole]-5'-carboxamide or a pharmaceutically acceptable salt thereof and ibrutinib or a pharmaceutically acceptable salt thereof in combination, and a treatment method using these compounds or salts in combination.

17 Claims, 2 Drawing Sheets

(56) References Cited

OTHER PUBLICATIONS

Ding et al., "Structure-Based Design of Potent Non-Peptide MDM2 inhibitors," *J. Am. Chem. Soc.*, (2005), 127:10130-10131.

Ding et al., "Structure-Based Design of Spiro-oxindoles as Potent, Specific Small-Molecule Inhibitors of the MDM2-p53 Interaction," *J. Med. Chem.*, (2006), 49:3432-3435.

Hardcastle et al., "Small-Molecule Inhibitors of the MDM2-p53 Protein-Protein Interaction Based on an Isoindolinone Scaffold," *J. Med. Chem.*, (2006), 49:6209-6221.

Honigberg et al., "The Bruton tyrosine kinase inhibitor PCI-32765 blocks B-cell activation and is efficacious in models of autoimmune disease and B-cell malignancy," *PNAS*, Jul. 20, 2010, 107(29):13075-13080.

Ishizawa et al., "ONC201 Exerts p53-Independent Cytotoxicity Through TRAIL and DR5 Induction in Mantle Cell Lymphomas," *Blood*, (2013), 122:3822.

Matthews Griner et al., "High-throughput combinatorial screening identifies drugs that cooperate with ibrutinib to kill activated B-cell-like diffuse large B-cell lymphoma cells," *PNAS*, Feb. 11, 2014, 111(6):2349-2354.

Schaeffer et al., "Tec family kinases in lymphocyte signaling and function," *Curr. Opin. Immunol.*, (2000), 12:282-288.

Yang et al., "Bruton Tyrosine Kinase Is a Therapeutic Target in Stem-like Cells from Multiple Myeloma," *Cancer Res.*, (2015), 75(3):594-604.

Yu et al., "Potent and Orally Active Small-Molecule Inhibitors of the MDM2-p53 Interaction," *J. Med. Chem.*, (2009), 52:7970-7973.

\* cited by examiner

TREATMENT METHOD BY COMBINED USE OF MDM2 INHIBITOR AND BTK INHIBITOR

This application is a national stage application under 35 U.S.C. § 371 of International Application No. PCT/JP2016/061762, filed Apr. 12, 2016, entitled "TREATMENT METHOD COMBINING MDM2 INHIBITOR AND BTK INHIBITOR," which claims priority to Japanese Patent Application No. 2015-082013, filed Apr. 13, 2015.

TECHNICAL FIELD

The present invention relates to a medicament and a method for treating cancer comprising a compound having murine double minute 2 (MDM2) inhibiting activity and a compound having Bruton's tyrosine kinase (BTK) inhibiting activity in combination.

BACKGROUND ART p53 is known as an important factor for inhibiting canceration of cells. p53 is a transcription factor that induces the expression of genes involved in the cell cycle and cellular apoptosis in response to various stresses. p53 is thought to inhibit canceration of cells by a transcription regulating function thereof. In fact, deletion or mutation of the p53 gene is observed in about half of human cancer cases.

Meanwhile, overexpression of murine double minute 2 (MDM2), a type of E3 ubiquitin ligase, is known as a factor for canceration of cells that are cancerated in spite of the presence of normal p53. MDM2 is a protein whose expression is induced by p53. MDM2 negatively regulates p53 by binding to the transcription activity domain of p53 to decrease the transcription activity of p53, exporting p53 out of the nucleus, and mediating degradation of p53 by acting as an ubiquitination ligase against p53. Therefore, it is thought that inactivation of functions of and degradation of p53 are promoted in cells in which MDM2 is overexpressed, resulting in canceration (Non Patent Document 1).

Paying attention to such functions of MDM2, many approaches have been attempted using substances that inhibit the suppression of p53 functions by MDM2 as candidate anti-tumor agents. Examples of MDM2 inhibitors targeting the MDM2-p53 binding site have been reported, which include spirooxindole derivatives (Patent Documents 1 to 15 and Non Patent Documents 1 to 3), indole derivatives (Patent Document 16), pyrrolidine-2-carboxamide derivatives (Patent Document 17), pyrrolidinone derivatives (Patent Document 18), isoindolinone derivatives (Patent Document 19 and Non Patent Document 4) and dispiropyrrolidine compounds (Patent Document 20).

Bruton's tyrosine kinase (BTK) is an important signaling enzyme that belongs to the Tec family of non-receptor tyrosine kinases and is expressed in all hematopoietic cells except for T lymphocytes and natural killer cells (Non Patent Document 5). BTK plays an essential role in the B cell signaling pathway, which links cell surface B cell receptor (BCR) stimuli to downstream intracellular response. BTK is an important regulatory factor for the development, activation, signal transduction, and survival of B cells.

Ibrutinib (PCI-32765) is a small molecule compound having a BTK inhibitory effect and is reportedly effective for B cell tumors and autoimmune diseases (Patent Documents 21 and 22 and Non Patent Documents 6 and 7). In Europe and the U.S., ibrutinib is used as an anti-tumor drug for mantle cell lymphoma (MCL) and chronic lymphatic leukemia (CLL) as indications and is also under development for diffuse large B cell lymphoma (DLBCL) and multiple myeloma (MM) as indications (Non Patent Documents 7 and 8).

CITATION LIST

Patent Documents

Patent Document 1: WO2006/091646
Patent Document 2: WO2006/136606
Patent Document 3: WO2007/104664
Patent Document 4: WO2007/104714
Patent Document 5: WO2008/034736
Patent Document 6: WO2008/036168
Patent Document 7: WO2008/055812
Patent Document 8: WO2008/141917
Patent Document 9: WO2008/141975
Patent Document 10: WO2009/077357
Patent Document 11: WO2009/080488
Patent Document 12: WO2010/084097
Patent Document 13: WO2010/091979
Patent Document 14: WO2010/094622
Patent Document 15: WO2010/121995
Patent Document 16: WO2008/119741
Patent Document 17: WO2010/031713
Patent Document 18: WO2010/028862
Patent Document 19: WO2006/024837
Patent Document 20: WO2012/121361
Patent Document 21: WO2008/039218
Patent Document 22: WO2013/059738

Non Patent Documents

Non Patent Document 1: J. Am. Chem. Soc., 2005, 127, 10130-10131
Non Patent Document 2: J. Med. Chem., 2006, 49, 3432-3435
Non Patent Document 3: J. Med. Chem., 2009, 52, 7970-7973
Non Patent Document 4: J. Med. Chem., 2006, 49, 6209-6221
Non Patent Document 5: Curr. Opin. Immunol., 2000, 12, 282-288
Non Patent Document 6: PNAS, 2010, 107, 13075-13080
Non Patent Document 7: Drugs, 2014, 74, 263-271
Non Patent Document 8: Can. Res., 2015, 75, 594-604

SUMMARY OF INVENTION

Technical Problem

An object of the present invention is to provide a medicament and a method for treating cancer comprising a compound having MDM2 inhibiting activity and a compound having BTK inhibiting activity in combination.

Solution to the Problem

As a result of extensive studies, the present inventors have found that use of (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro [cyclohexane-1,2'-pyrrolidine-3',3"-indole]-5'-carboxamide, which is a compound having MDM2 inhibiting activity, or a pharmaceutically acceptable salt thereof and ibrutinib, which is a compound having BTK inhibiting activity, or a pharmaceutically acceptable salt thereof in combination particularly produces an excellent anti-tumor effect and accomplished the present invention.

Specifically, the present invention relates to the following [1] to [15]:

[1] A medicament for cancer treatment comprising (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide or a pharmaceutically acceptable salt thereof and ibrutinib or a pharmaceutically acceptable salt thereof which are administered in combination.

[2] A medicament according to [1], wherein the (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide or the pharmaceutically acceptable salt thereof and ibrutinib or the pharmaceutically acceptable salt thereof are separately contained as active ingredients in different formulations and administered at the same time or different times.

[3] A medicament according to [1], wherein the (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide or the pharmaceutically acceptable salt thereof and ibrutinib or the pharmaceutically acceptable salt thereof are contained in a single formulation.

[4] A medicament according to [1], wherein the medicament is a kit formulation comprising the (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro [cyclohexane-1,2'-pyrrolidine-3',3"-indole]-5'-carboxamide or the pharmaceutically acceptable salt thereof and ibrutinib or the pharmaceutically acceptable salt thereof.

[5] A method for treating cancer comprising administering (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide or a pharmaceutically acceptable salt thereof and ibrutinib or a pharmaceutically acceptable salt thereof in combination.

[6] A medicament according to any one of [1] to [4], wherein the salt of (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide is p-toluenesulfonate.

[7] A treatment method according to [5], wherein the salt of (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide is p-toluenesulfonate.

[8] A medicament according to any one of [1] to [4] and [6], wherein the cancer is a hematological malignancy, brain tumor, head/neck region cancer, esophageal cancer, stomach cancer, appendix cancer, colon cancer, anus cancer, gallbladder cancer, bile duct cancer, pancreatic cancer, gastrointestinal stromal tumor, lung cancer, liver cancer, mesothelioma, thyroid gland cancer, renal cancer, prostate cancer, neuroendocrine tumor, melanoma, breast cancer, uterine body cancer, uterine cervix cancer, ovarian cancer, osteosarcoma, soft tissue sarcoma, Kaposi's sarcoma, myosarcoma, urinary bladder cancer or testicular cancer.

[9] A treatment method according to [5] or [7], wherein the cancer is a hematological malignancy, brain tumor, head/neck region cancer, esophageal cancer, stomach cancer, appendix cancer, colon cancer, anus cancer, gallbladder cancer, bile duct cancer, pancreatic cancer, gastrointestinal stromal tumor, lung cancer, liver cancer, mesothelioma, thyroid gland cancer, renal cancer, prostate cancer, neuroendocrine tumor, melanoma, breast cancer, uterine body cancer, uterine cervix cancer, ovarian cancer, osteosarcoma, soft tissue sarcoma, Kaposi's sarcoma, myosarcoma, urinary bladder cancer or testicular cancer.

[10] A medicament according to any one of [1] to [4] and [6], wherein the cancer is a hematological malignancy.

[11] A treatment method according to [5] or [7], wherein the cancer is a hematological malignancy.

[12] A medicament according to [10], wherein the hematological malignancy is chronic lymphatic leukemia (CLL), small lymphocytic lymphoma (SLL), high-risk CLL, non-CLL/SLL lymphoma, follicular lymphoma (FL), diffuse large B cell lymphoma (DLBCL), mantle cell lymphoma (MCL), Waldenstrom's macroglobulinemia, multiple myeloma (MM), marginal zone lymphoma, Burkitt's lymphoma, non-Burkitt high-grade B cell lymphoma, extranodal marginal zone B cell lymphoma, acute or chronic myelogenous (myelocytic) leukemia, myelodysplastic syndrome or acute lymphoblastic leukemia.

[13] A treatment method according to [11], wherein the hematological malignancy is chronic lymphatic leukemia (CLL), small lymphocytic lymphoma (SLL), high-risk CLL, non-CLL/SLL lymphoma, follicular lymphoma (FL), diffuse large B cell lymphoma (DLBCL), mantle cell lymphoma (MCL), Waldenstrom's macroglobulinemia, multiple myeloma (MM), marginal zone lymphoma, Burkitt's lymphoma, non-Burkitt high-grade B cell lymphoma, extranodal marginal zone B cell lymphoma, acute or chronic myelogenous (myelocytic) leukemia, myelodysplastic syndrome or acute lymphoblastic leukemia.

[14] A medicament according to any one of [1] to [4], [6], [8], [10] and [12], wherein the cancer is cancer confirmed to be MDM2 inhibitor-sensitive using a gene signature.

[15] A treatment method according to any one of [5], [7], [9], [11] and [13], wherein the cancer is cancer confirmed to be MDM2 inhibitor-sensitive using a gene signature.

Advantageous Effects of Invention

The present invention is useful as a method for treating cancer and/or an anti-cancer agent having little adverse reaction (e.g., weight loss) and high effects.

BRIEF DESCRIPTION OF DRAWINGS

FIG. 1-1 is a diagram showing in vivo effects of combined use of (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide p-toluenesulfonate (Compound A) and ibrutinib on a tumor derived from subcutaneously transplanted ABC-type (activated B cell type) DLBCL cell line TMD-8 cells in mice, and body weight change caused by combined administration thereof. The symbol × depicts an untreated control group, the symbol open circle depicts 100 mg/kg ibrutinib, the symbol filled circle depicts 200 mg/kg ibrutinib, the symbol open triangle depicts 25 mg/kg Compound A, the symbol open square depicts 25 mg/kg Compound A+100 mg/kg ibrutinib, and the symbol filled square depicts 25 mg/kg Compound A+200 mg/kg ibrutinib. The horizontal axis shows the number of days after tumor inoculation. The vertical axis of the upper panel shows estimated tumor volume calculated from tumor size. The vertical axis of the lower panel shows body weight change % relative to body weight on the first day of administration. The symbol filled triangle on the horizontal axis depicts the administration day of each compound. The error bar represents SE for the upper panel and SD for the lower panel.

FIG. 1-2 is a diagram showing in vivo effects of combined use of (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide p-toluenesulfonate (Compound A) and ibrutinib on a tumor derived from subcutaneously transplanted ABC-type (activated B cell type) DLBCL cell line TMD-8 cells in mice, and body weight change caused by combined administration thereof. The symbol × depicts an untreated control group, the symbol open circle depicts 100 mg/kg ibrutinib, the symbol filled circle depicts 200 mg/kg ibrutinib, the symbol open triangle depicts 50 mg/kg Compound A, the symbol open square depicts 50 mg/kg Compound A +100 mg/kg ibrutinib, and the symbol filled square depicts 50 mg/kg Compound A +200 mg/kg ibrutinib. The horizontal axis shows the number of days after tumor inoculation. The vertical axis of the upper panel shows estimated tumor volume calculated from tumor size. The vertical axis of the lower panel shows body weight change % relative to body weight on the first day of administration. The symbol filled triangle on the horizontal axis depicts the administration day of each compound. The error bar represents SE for the upper panel and SD for the lower panel.

DESCRIPTION OF EMBODIMENTS

In the present invention, the (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide is the compound of Example 70 in WO2012/121361. This compound can be produced by a method described in WO2012/121361 (WO2012/121361 is incorporated herein by reference in its entirety).

In the present invention, ibrutinib is (R)-1-(3-(4-amino-3-(4-phenoxyphenyl)-1H-pyrazolo[3,4-d]pyrimidin-1-yl)piperidin-1-yl)prop-2-en-1-one and is also referred to as PCI-32765 or Imbruvica®. This compound can be produced by a method described in WO2008/039218 (WO2008/039218 is incorporated herein by reference in its entirety).

In the present invention, the (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide and ibrutinib may be various pharmaceutically acceptable salts.

Examples of the salts can include: hydrohalides such as hydrochloride and hydroiodide; inorganic acid salts such as nitrate, perchlorate, sulfate and phosphate; lower alkanesulfonates such as methanesulfonate, trifluoromethanesulfonate and ethanesulfonate; arylsulfonates such as benzenesulfonate and p-toluenesulfonate; organic acid salts such as formic acid, acetic acid, malic acid, fumarate, succinate, citrate, tartrate, oxalate and maleate; amino acid salts such as ornithine salt, glutamate and aspartate; alkali metal salts such as sodium salt, potassium salt and lithium salt; alkaline earth metal salts such as calcium salt and magnesium salt; inorganic salts such as ammonium salt; and organic amine salts such as dibenzylamine salt, morpholine salt, phenylglycine alkyl ester salt, ethylenediamine salt, N-methylglucamine salt, diethylamine salt, triethylamine salt, cyclohexylamine salt, dicyclohexylamine salt, N,N'-dibenzylethylenediamine salt, diethanolamine salt, N-benzyl-N-(2-phenylethoxy)amine salt, piperazine salt, tetramethylammonium salt and tris(hydroxymethyl)aminomethane salt.

The salt of the (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide is preferably p-toluenesulfonate.

In the present invention, the (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide and ibrutinib or their pharmaceutically acceptable salts may each be present in a free or solvate form. The compounds or the salts thereof may be present in a hydrate form, for example, by absorbing moisture in the air. The solvate is not particularly limited so long as it is pharmaceutically acceptable. Specifically, the solvate is preferably a hydrate, an ethanol solvate or the like. Moreover, the compound may be in an N-oxide form when containing a nitrogen atom. These solvate and N-oxide forms are also included in the present invention.

The (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide and ibrutinib or their pharmaceutically acceptable salts may have stereoisomers depending on their structures. The compounds or the salts also encompass all these stereoisomers and mixtures of these stereoisomers in any ratio. The stereoisomers are as defined in 1996 IUPC, Pure and Applied Chemistry 68, 2193-2222. When the (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide and ibrutinib or their pharmaceutically acceptable salts are each present as tautomers, these tautomers may be present in equilibrium or a certain form may be dominantly present. All these cases are included in the scope of the present invention. The tautomers refer to isomers resulting from the shift of a proton of one atom of the molecule to another atom.

The (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide and ibrutinib or their pharmaceutically acceptable salts may each be a "pharmaceutically acceptable prodrug compound" that is converted to the desired compound through enzymatic oxidation, reduction, hydrolysis or the like or through hydrolysis or the like induced by gastric acid or the like, due to a reaction induced by an enzyme, gastric acid or the like under physiological conditions in vivo.

Examples of the prodrug include compounds obtained by acylation, alkylation or phosphorylation.

Prodrugs of the compounds can be produced according to a method known in the art. Moreover, prodrugs of the compounds also include those converted to the desired compounds under physiological conditions as described in "Development of Pharmaceutical Products", vol. 7, Molecule Design, p. 163-198, Hirokawa-Shoten Ltd. (1990).

In the present invention, the terms "tumor" and "cancer" are used interchangeably. Furthermore, in the present invention, tumor, malignant tumor, cancer, malignant neoplasm, carcinoma, sarcoma, and the like may be collectively referred to as "tumor" or "cancer".

In the present invention, "gene signature" means a single gene or a gene group consisting of a plurality of genes, whose expression pattern is characteristic of a biological phenotype or a medical condition, such as morbidity of a certain disease, response to a certain medicament, or prognosis of a certain disease.

In the present invention, "biological sample" refers to tissues, liquids or cells isolated from an individual, or a mixture thereof. Examples thereof can include, but are not limited to, tumor biopsy, spinal fluid, pleural fluid, intra-abdominal fluid, lymph, skin sections, blood, urine, feces, sputum, respiratory organ, intestinal tract, genitourinary tract, saliva, milk, digestive organ, and cells collected therefrom. Preferred examples of "biological sample" can include a portion of test subject-derived resected tissues obtained during surgery performed for the purpose of treating a cancer disease, a portion of tissues collected by biopsy or the like from a test subject suspected of having a cancer disease, and cells derived from pleural fluid or intra-abdominal fluid.

The biological sample may be protein extracts or nucleic acid extracts prepared from tissues, liquids or cells isolated from an individual, or a mixture thereof, etc. The protein extracts or the nucleic acid extracts can be prepared by use of a protein preparation method or a nucleic acid preparation method known per se in the art.

One aspect of the present invention relates to a medicament for cancer treatment comprising (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide or a pharmaceutically acceptable salt thereof and ibrutinib or a pharmaceutically acceptable salt thereof which are administered in combination.

In the present invention, a "medicament" comprising (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide or a pharmaceutically acceptable salt thereof and ibrutinib or a pharmaceutically acceptable salt thereof "which are administered in combination" is a medicament based on the assumption that both the drugs are administered in combination.

In the present invention, the "administration in combination" of (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide or a pharmaceutically acceptable salt thereof and ibrutinib or a pharmaceutically acceptable salt thereof means that both the drugs are incorporated into the body of a recipient in a given period. A formulation containing both the drugs in a single formulation may be administered, or the drugs may be prepared into separate formulations and separately administered. In the case of preparing separate formulations, the timing of their administration is not particularly limited. The separate formulations may be administered at the same time or may be administered at different times or on different days in a staggered manner. In the case of administering the (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide or the pharmaceutically acceptable salt thereof and ibrutinib or the pharmaceutically acceptable salt thereof at different times or on different days, the order of their administration is not particularly limited. Usually, these formulations are administered according to their respective administration methods. Therefore, these formulations may be administered in the same number of doses or may be administered in a different number of doses. Also, in the case of preparing separate formulations, the respective administration methods (administration routes) of the formulations may be the same as each other, or these formulations may be administered by different administration methods (administration routes). Both the drugs do not have to exist at the same time in the body and may be incorporated into the body over a given period (e.g., 1 month, preferably 1 week, more preferably a few days, even more preferably 1 day). One of the active ingredients may have disappeared from the body at the time of administration of the other active ingredient.

Examples of a dosage form of the medicament of the present invention include 1) administration of a single formulation comprising (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide or a pharmaceutically acceptable salt thereof and ibrutinib or a pharmaceutically acceptable salt thereof, 2) concurrent administration through the same administration route of two formulations separately prepared from (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide or a pharmaceutically acceptable salt thereof and ibrutinib or a pharmaceutically acceptable salt thereof, 3) administration in a staggered manner through the same administration route of two formulations separately prepared from (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide or a pharmaceutically acceptable salt thereof and ibrutinib or a pharmaceutically acceptable salt thereof, 4) concurrent administration through different administration routes of two formulations separately prepared from (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide or a pharmaceutically acceptable salt thereof and ibrutinib or a pharmaceutically acceptable salt thereof, and 5) administration in a staggered manner through different administration routes of two formulations separately prepared from (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide or a pharmaceutically acceptable salt thereof and ibrutinib or a pharmaceutically acceptable salt thereof.

In the present invention, the two different formulations may be in the form of a kit comprising these formulations.

A medicament according to the present invention can contain (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide or a pharmaceutically acceptable salt thereof and/or ibrutinib or a pharmaceutically acceptable salt thereof and a pharmaceutically acceptable carrier and can be administered as various injections such as intravenous injection, intramuscular injection, and subcutaneous injection or by various methods such as oral administration or percutaneous administration. A pharmaceutically acceptable carrier means a pharmaceutically acceptable material that is involved in transport of the compound of the present invention or a composition containing the compound of the present invention (e.g., an excipient, a diluent, an additive and a solvent) from a given organ to another organ.

A formulation can be prepared by selecting a suitable formulation form (e.g., oral formulation or injection) depending on the administration method and using various methods conventionally used for preparing a formulation. Examples of oral formulations can include tablets, powders, granules, capsules, pills, lozenges, solutions, syrups, elixirs, emulsions and oily or aqueous suspensions. In oral administration, the free compound or a salt form may be used. An aqueous formulation can be prepared by forming an acid adduct with a pharmaceutically acceptable acid or by forming an alkali metal salt such as sodium. As an injection, a stabilizer, a preservative, a dissolving aid, and the like can be used in the formulation. After filling a solution that may contain these aids and the like in a vessel, a formulation for use may be prepared as a solid formulation by lyophilization or the like. Furthermore, one dose may be filled in one vessel, or two or more doses may be filled in a vessel.

Examples of solid formulations include tablets, powders, granules, capsules, pills and lozenges. These solid formulations may contain pharmaceutically acceptable additives together with a compound of the present invention. Examples of additives include fillers, extenders, binders, disintegrating agents, dissolution promoting agents, skin wetting agents and lubricants. These additives can be selected and mixed as required to prepare a formulation.

Examples of liquid formulations include solutions, syrups, elixirs, emulsions and suspensions. Examples of additives include suspending agents and emulsifiers. These additives can be selected and mixed as required to prepare a formulation.

Examples of pharmaceutical materials can include, but are not limited to: amino acids such as glycine, alanine, glutamine, asparagine, arginine and lysine; antimicrobial agents; antioxidants such as ascorbic acid, sodium sulfate and sodium bisulfite; buffers such as phosphate, citrate or borate buffers, sodium bicarbonate and Tris-HCl solutions; fillers such as mannitol and glycine; chelating agents such as ethylenediaminetetraacetic acid (EDTA); complexing agents such as caffeine, polyvinylpyrrolidine, β-cyclodextrin and hydroxypropyl-β-cyclodextrin; bulking agents such as glucose, mannose and dextrin; other carbohydrates such as monosaccharides and disaccharides; coloring agents; corrigents; diluents; emulsifiers; hydrophilic polymers such as polyvinylpyrrolidine; low-molecular-weight polypeptides; salt-forming counterions; antiseptics such as benzalkonium chloride, benzoic acid, salicylic acid, thimerosal, phenethyl alcohol, methylparaben, propylparaben, chlorhexidine, sorbic acid and hydrogen peroxide; solvents such as glycerin, propylene glycol and polyethylene glycol; sugar alcohols such as mannitol and sorbitol; suspending agents; surfactants such as sorbitan ester, polysorbates such as polysorbate 20 and polysorbate 80, triton, tromethamine, lecithin and cholesterol; stability enhancers such as sucrose and sorbitol; elasticity enhancers such as sodium chloride, potassium chloride, mannitol and sorbitol; transport agents; excipients; and/or pharmaceutical additives. The amount of these pharmaceutical materials added is preferably 0.01 to 100 times, particularly, 0.1 to 10 times the weight of the drug. The recipe of a preferred pharmaceutical composition in a formulation can be appropriately determined by those skilled in the art according to an applicable disease, an applicable administration route, etc.

An excipient or a carrier in a pharmaceutical composition may be liquid or solid. Appropriate excipients or carriers may be other materials usually used in injectable water, physiological saline, artificial cerebrospinal fluid, and parenteral administration. Neutral physiological saline or physiological saline containing serum albumin may be used as a carrier. The pharmaceutical composition can contain a Tris buffer of pH 7.0 to 8.5, an acetate buffer of pH 4.0 to 5.5, or a citrate buffer of pH 3.0 to 6.2. These buffers can also contain sorbitol or other compounds.

Preferred examples of the formulation of ibrutinib or the pharmaceutically acceptable salt thereof include formulations described in WO2008/039218, formulations described in WO2010/009342, formulations described in WO2011/153514, formulations described in WO2013/059738, formulations described in WO2014/071231, formulations described in WO2013/159745, formulations described in WO2014/168975, formulations described in WO2014/194254 and formulations described in WO2015/017812 (these documents are incorporated herein by reference in their entirety). More preferred examples thereof include capsule formulations containing croscarmellose sodium, magnesium stearate, crystalline cellulose and sodium lauryl sulfate.

The medicament of the present invention can be used in cancer treatment of mammals, particularly, humans. The dose and the administration interval of the medicament of the present invention can be suitably selected depending on the site of the disease, the patient's height, body weight, sex, or medical history, according to a physician's judgment. When the medicament of the present invention is administered to a human, the dose range is approximately 0.01 to 500 mg/kg body weight, preferably, approximately 0.1 to 100 mg/kg body weight, per day with respect to one type of active ingredient. Preferably, the active ingredient of the present invention is administered to a human once a day, or the dose is divided two to four times, and administration is repeated at an appropriate interval. Furthermore, the daily dose may exceed the above-mentioned dose at a physician's discretion, if necessary.

For examples of the administration method of ibrutinib or the pharmaceutically acceptable salt thereof, see a method described in WO2008/039218, a method described in WO2010/009342, a method described in WO2011/153514, a method described in WO2013/059738, a method described in WO2014/071231, a method described in WO2013/159745, a method described in WO2014/168975, a method described in WO2014/194254 and a method described in WO2015/017812, all of which are incorporated herein by reference in their entirety. This active ingredient may be administered once a day for 1 week, 2 weeks, 3 weeks, 4 weeks or 5 weeks.

The type of cancer to be treated is not particularly limited as long as the cancer is confirmed to be sensitive to treatment by combined use of the present invention. Examples thereof include a hematological malignancy, brain tumor, head/neck region cancer, esophageal cancer, stomach cancer, appendix cancer, colon cancer, anus cancer, gallbladder cancer, bile duct cancer, pancreatic cancer, gastrointestinal stromal tumor, lung cancer, liver cancer, mesothelioma, thyroid gland cancer, renal cancer, prostate cancer, neuroendocrine tumor, melanoma, breast cancer, uterine body cancer, uterine cervix cancer, ovarian cancer, osteosarcoma, soft tissue sarcoma, Kaposi's sarcoma, myosarcoma, urinary bladder cancer and testicular cancer.

Among them, a hematological malignancy is preferred. Examples of the hematological malignancy include chronic lymphatic leukemia (CLL), small lymphocytic lymphoma (SLL), high-risk CLL, non-CLL/SLL lymphoma, follicular lymphoma (FL), diffuse large B cell lymphoma (DLBCL), mantle cell lymphoma (MCL), Waldenstrom's macroglobulinemia, multiple myeloma (MM), marginal zone lymphoma, Burkitt's lymphoma, non-Burkitt high-grade B cell lymphoma, extranodal marginal zone B cell lymphoma, acute or chronic myelogenous (myelocytic) leukemia, myelodysplastic syndrome and acute lymphoblastic leukemia.

From another viewpoint, the type of cancer to be treated is preferably a cancer sensitive to an MDM2 inhibitor and is more preferably a cancer having wild-type TP53.

As methods for confirming TP53 to be wild-type, examples thereof include a microarray method using a probe specific for a mutated DNA sequence (AmpliChip p53, Roche Molecular Systems, Inc., etc., http://www.ncbi.nlm.nih.gov/pubmed/21319261), PCR using a probe specific for a mutated DNA sequence (qBiomarker Somatic Mutation PCR Arrays, Qiagen N.V., etc.), a method of reading the p53 gene sequence using a Sanger sequencer (http://p53.iarc.fr/Download/TP53_DirectSequencing_IARC.pdf), and a method of reading the p53 gene sequence using a next-generation sequencer (TruSeq Amplicon—Cancer Panel, Illumina http://www.illuminakk.co.jp/products/truseq_amplicon_cancer_pa nel.ilmn, Oncomine® Cancer Research Panel, Life Technologies Corp., http://www.lifetechnologies.com/jp/ja/home/clinical/preclinica 1-companion-diagnostic-development/oncomine-cancer-research-panel-workflow.html, etc.).

A method using a gene signature can also be preferably used as a method for predicting sensitivity for an MDM2 inhibitor. Examples of the gene signature for predicting sensitivity for an MDM2 inhibitor include, but are not particularly limited to, a gene group described in WO2014/020502 (WO2014/020502 is incorporated herein by reference in its entirety). More specifically, a gene group comprising at least one gene selected from the group consisting of MDM2, CDKN1A, ZMAT3, DDB2, FDXR, RPS27L, BAX, RPM2B, SESN1, CCNG1, XPC, TNFSF10B and AEN (the gene group may comprise all of these genes) can be preferably used. Other examples thereof include a gene group described in WO2015/000945 (WO2014/000945 is incorporated herein by reference in its entirety). More specifically, a gene group comprising at least one gene selected from the group consisting of BAX, RPS27L, EDA2R, XPC, DDB2, FDXR, MDM2, CDKN1A, TRIAP1, BBC3, CCNG1, TNFRSF10B and CDKN2A (the gene group may comprise all of these genes) can be preferably used. The number of genes contained in the gene group is not limited. A sensitive signature that allows the cancer to be confirmed as sensitive to an MDM2 inhibitor when the gene contained in the gene signature is highly expressed can be preferably used.

The medicament according to the present invention may be used in combination with an additional anti-tumor agent. Examples thereof include anti-tumor antibiotics, anti-tumor plant constituents, BRMs (biological response modifiers), hormones, vitamins, anti-tumor antibodies, molecular target drugs, alkylating agents, metabolic antagonists and other anti-tumor agents.

More specifically, examples of alkylating agents include: alkylating agents such as nitrogen mustard, nitrogen mustard N-oxide, bendamustine and chlorambucil; aziridine alkylating agents such as carboquone and thiotepa; epoxide alkylating agents such as dibromomannitol and dibromodulcitol; nitrosourea alkylating agents such as carmustine, lomustine, semustine, nimustine hydrochloride, streptozocin, chlorozotocin and ranimustine; and busulfan, improsulfan tosylate, temozolomide and dacarbazine.

Various examples of metabolic antagonists include: purine metabolic antagonists such as 6-mercaptopurine, 6-thioguanine and thioinosine; pyrimidine metabolic antagonists such as fluorouracil, tegafur, tegafur-uracil, carmofur, doxifluridine, broxuridine, cytarabine and enocitabine; and folic acid metabolic antagonists such as methotrexate and trimetrexate.

Examples of anti-tumor antibiotics include: mitomycin C, bleomycin, peplomycin, daunorubicin, aclarubicin, doxorubicin, idarubicin, pirarubicin, THP-adriamycin, 4'-epidoxorubicin and epirubicin; and chromomycin A3 and actinomycin D.

Examples of anti-tumor plant constituents and their derivatives include: vinca alkaloids such as vindesine, vincristine and vinblastine; taxanes such as paclitaxel, docetaxel and cabazitaxel; and epipodophyllotoxins such as etoposide and teniposide.

Examples of BRMs include tumor necrosis factors and indomethacin.

Examples of hormones include hydrocortisone, dexamethasone, methylprednisolone, prednisolone, prasterone, betamethasone, triamcinolone, oxymetholone, nandrolone, metenolone, fosfestrol, ethinylestradiol, chlormadinone, mepitiostane and medroxyprogesterone.

Examples of vitamins include vitamin C and vitamin A.

Examples of anti-tumor antibodies and molecular target drugs include trastuzumab, rituximab, cetuximab, nimotuzumab, denosumab, bevacizumab, infliximab, ipilimumab, nivolumab, pembrolizumab, avelumab, pidilizumab, atezolizumab, ramucirumab, imatinib mesylate, dasatinib, gefitinib, erlotinib, osimertinib, sunitinib, lapatinib, dabrafenib, trametinib, cobimetinib, pazopanib, palbociclib, panobinostat, sorafenib, crizotinib, vemurafenib, quizartinib, bortezomib, carfilzomib, ixazomib and gilteritinib.

Examples of other anti-tumor agents include cisplatin, carboplatin, oxaliplatin, tamoxifen, letrozole, anastrozole, exemestane, toremifene citrate, fulvestrant, bicalutamide, flutamide, mitotane, leuprorelin, goserelin acetate, camptothecin, ifosfamide, cyclophosphamide, melphalan, L-asparaginase, aceglatone, sizofiran, picibanil, procarbazine, pipobroman, neocarzinostatin, hydroxyurea, ubenimex, azacitidine, decitabine, thalidomide, lenalidomide, pomalidomide, eribulin, tretinoin and krestin.

More specific examples of the combination include combination with CHOP (cyclophosphamide, hydroxydoxorubicin, vincristine and prednisone), combination with EPOCH (etoposide, prednisone, vincristine, cyclophosphamide and hydroxydoxorubicin), combination with hyper-CVAD (cyclophosphamide, vincristine, hydroxydoxorubicin and dexamethasone), combination with ICE (ifosfamide, carboplatin and etoposide), combination with DHAP (high-dose cytarabine (ara-C), dexamethasone and cisplatin), combination with ESHAP (etoposide, methylprednisolone, cytarabine (ara-C) and cisplatin), combination with anthracycline-based chemotherapy, combination with a histone deacetylase inhibitor, combination with a CYP3A4 inhibitor, combination with an anti-CD37 antibody, combination with a Bcl-2 inhibitor and combination with a PI 3-kinase inhibitor.

EXAMPLES

Hereinafter, the present invention will be specifically explained with reference to the Examples given below. However, the present invention is not limited to these examples, and they should not be construed in any limitative way.

(Test Example 1 Study on in Vivo Effect of Combined Use of Compound A and Ibrutinib)

ABC-type DLBCL cell line TMD-8 cells were suspended to $1\times10^8$ cells/mL using phosphate-buffered saline. 0.1 mL of the prepared cell suspension was subcutaneously transplanted to each NOD-SCID mouse (female, 6 weeks old). On 6 days after the tumor inoculation, after confirmation that the average tumor volume exceeded 100 mm³, the mice were grouped (6 mice per group) on the basis of their tumor volume values. 25 mg/kg or 50 mg/kg Compound A or 100 mg/kg or 200 mg/kg ibrutinib was orally administered by forced administration to the mice. For a combined use group, 25 mg/kg or 50 mg/kg Compound A and 100 mg/kg or 200 mg/kg ibrutinib were orally administered sequentially by forced administration. The administration was performed once a day for 5 consecutive days (18 to 22 days after the tumor inoculation) from the date of grouping (18 days after the tumor inoculation), and after a 2-day drug holiday, performed once a day for 4 consecutive days (25 to 28 days after the tumor inoculation). The major axis (mm) and minor axis (mm) of tumor were measured over time using an electronic digital caliper. Tumor growth inhibition % (TGI %) on the date of assessment (29 days after the tumor inoculation) calculated according to calculation formula (4) shown below was used in evaluation. Also, the body weights were measured over time using an automatic balance for small animals, and body weight change % was calculated according to calculation formula (5) shown below to study the influence of drug administration on the body weights. In addition, the results of the last body weight measurement were used in dose calculation.

$$TGI(\%)=(1-A/B)\times100 \tag{4}$$

A: Average tumor volume of the compound-administered group on the date of assessment (*)

B: Average tumor volume of the untreated control group on the date of assessment (*)

*: The tumor volume was calculated according to ½× [Major axis of tumor]×[Minor axis of tumor]×[Minor axis of tumor].

$$\text{Body weight change}(\%)=\text{Average body weight change \% of the individuals} \tag{5}$$

Body weight change % of each individual=(1−BWn/BWs)×100

BWn: Body weight on day n

BWs: Body weight on the start day of administration

Figure 11:
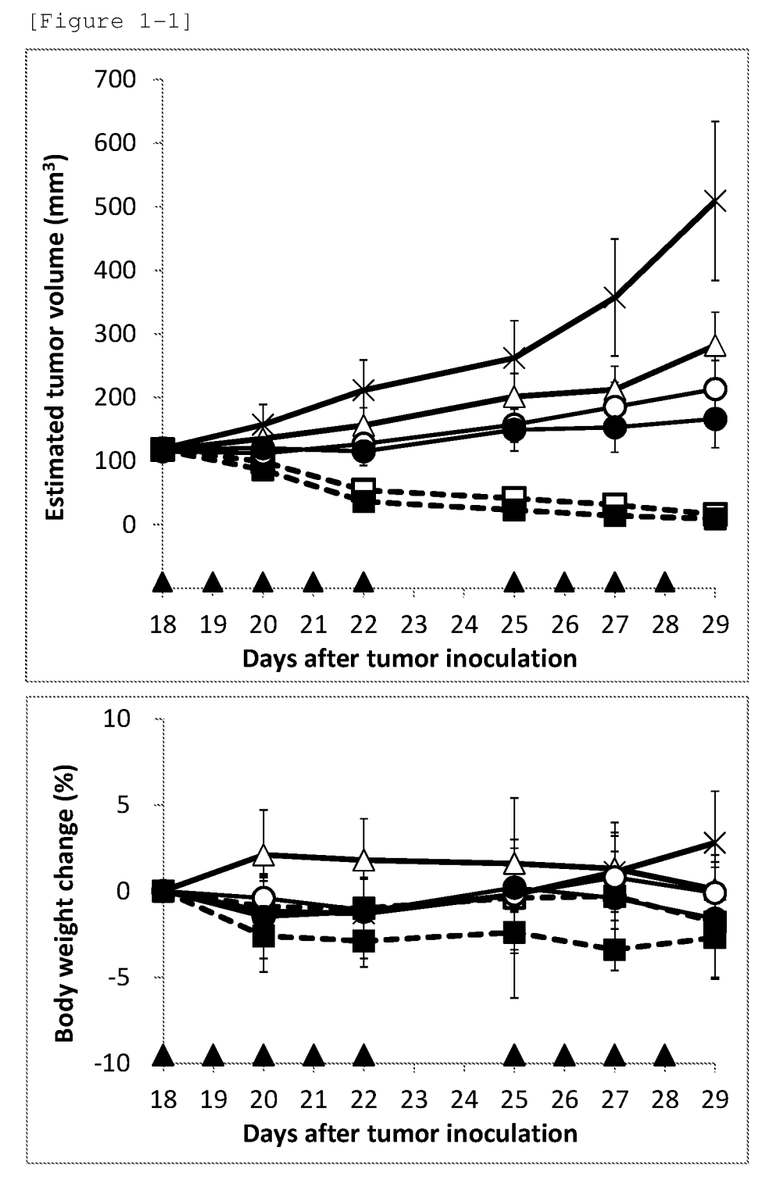
Figure 12:
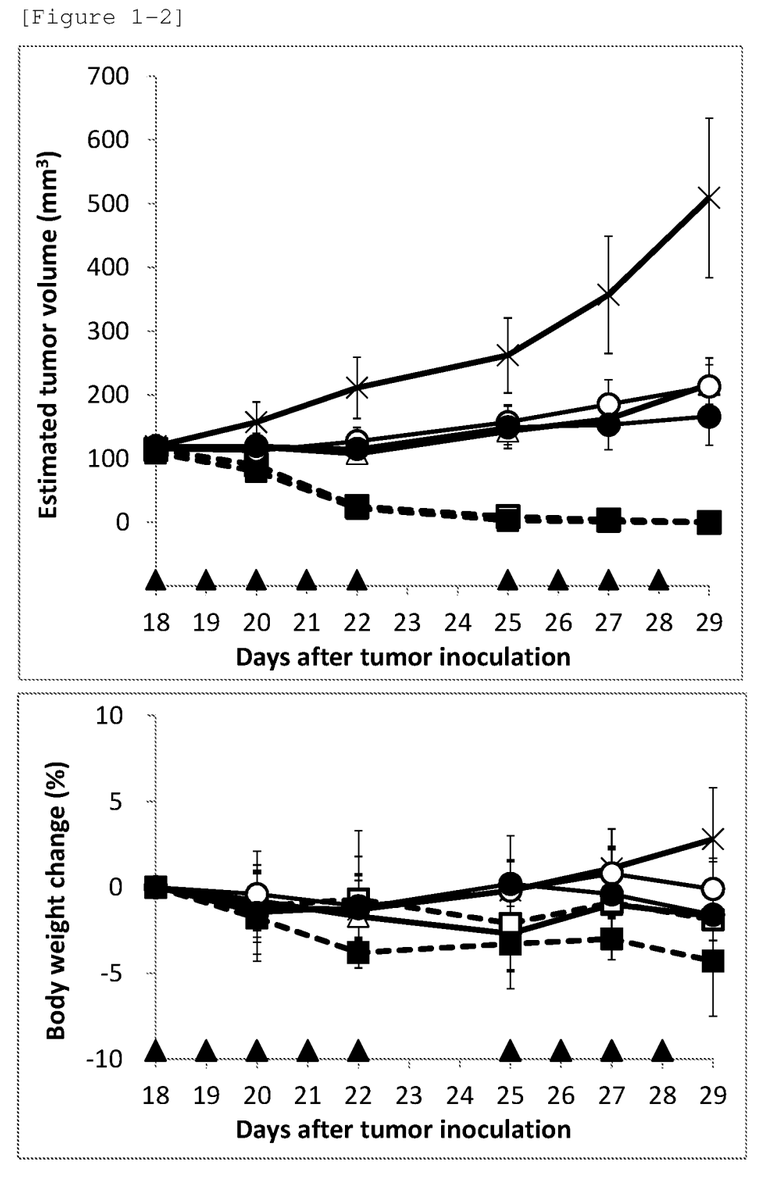

The results are shown in FIG. 1 and Tables 1 to 3.

TABLE 1

| Group | TGI (%) |
|---|---|
| Compound A 25 mg/kg | 45 |
| Compound A 50 mg/kg | 58 |
| Compound A 25 mg/kg + Ibrutinib 100 mg/kg | 97 |
| Compound A 50 mg/kg + Ibrutinib 100 mg/kg | 100 |
| Compound A 25 mg/kg + Ibrutinib 200 mg/kg | 98 |
| Compound A 50 mg/kg + Ibrutinib 200 mg/kg | 100 |
| Ibrutinib 100 mg/kg | 58 |
| Ibrutinib 200 mg/kg | 67 |

TABLE 2

Estimated tumor volume (mm³)

| Group | | Days after tumor inoculation | | | | | |
|---|---|---|---|---|---|---|---|
| | | 18 | 20 | 22 | 25 | 27 | 29 |
| 1. Untreated | average | 119 | 157 | 211 | 262 | 357 | 509 |
| | SE | 18 | 32 | 48 | 59 | 92 | 125 |
| 2. Compound A 25 mg/kg | average | 117 | 135 | 156 | 201 | 212 | 282 |
| | SE | 16 | 22 | 28 | 37 | 37 | 52 |
| 3. Compound A 50 mg/kg | average | 115 | 118 | 108 | 143 | 162 | 216 |
| | SE | 16 | 18 | 15 | 21 | 23 | 31 |
| 4. Compound A 25 mg/kg + Ibrutinib 100 mg/kg | average | 118 | 99 | 54 | 41 | 31 | 16 |
| | SE | 17 | 21 | 17 | 10 | 8 | 6 |
| 5. Compound A 50 mg/kg + Ibrutinib 100 mg/kg | average | 114 | 90 | 25 | 9 | 4 | 0 |
| | SE | 15 | 12 | 5 | 4 | 3 | 0 |
| 6. Compound A 25 mg/kg + Ibrutinib 200 mg/kg | average | 117 | 86 | 36 | 23 | 14 | 9 |
| | SE | 17 | 13 | 6 | 2 | 2 | 1 |
| 7. Compound A 50 mg/kg + Ibrutinib 200 mg/kg | average | 109 | 80 | 22 | 3 | 1 | 0 |
| | SE | 15 | 16 | 4 | 3 | 1 | 0 |
| 8. Ibrutinib 100 mg/kg | average | 115 | 112 | 127 | 157 | 185 | 213 |
| | SE | 16 | 13 | 22 | 27 | 39 | 45 |
| 9. Ibrutinib 200 mg/kg | average | 119 | 120 | 115 | 149 | 153 | 166 |
| | SE | 18 | 20 | 22 | 33 | 39 | 45 |

TABLE 3

| Group | | \multicolumn{6}{c}{Body weight change (%) Days after tumor inoculation} |
|---|---|---|---|---|---|---|---|
| | | 18 | 20 | 22 | 25 | 27 | 29 |
| 1. Untreated | average | 0.0 | −1.2 | −1.3 | −0.2 | 1.1 | 2.8 |
| | SD | 0.0 | 2.0 | 3.1 | 3.2 | 2.3 | 3.0 |
| 2. Compound A 25 mg/kg | average | 0.0 | 2.1 | 1.8 | 1.6 | 1.3 | 0.1 |
| | SD | 0.0 | 2.6 | 2.4 | 0.9 | 1.9 | 2.0 |
| 3. Compound A 50 mg/kg | average | 0.0 | −0.8 | −1.7 | −2.7 | −1.0 | −1.7 |
| | SD | 0.0 | 2.1 | 2.1 | 2.1 | 3.2 | 3.2 |
| 4. Compound A 25 mg/kg + Ibrutinib 100 mg/kg | average | 0.0 | −0.9 | −1.0 | −0.4 | −0.3 | −1.8 |
| | SD | 0.0 | 1.5 | 2.9 | 5.8 | 4.3 | 3.2 |
| 5. Compound A 50 mg/kg + Ibrutinib 100 mg/kg | average | 0.0 | −1.1 | −0.7 | −2.1 | −0.9 | −1.9 |
| | SD | 0.0 | 3.2 | 4.0 | 2.8 | 3.3 | 2.3 |
| 6. Compound A 25 mg/kg + Ibrutinib 200 mg/kg | average | 0.0 | −2.6 | −2.9 | −2.4 | −3.4 | −2.7 |
| | SD | 0.0 | 2.1 | 1.5 | 1.2 | 1.2 | 2.4 |
| 7. Compound A 50 mg/kg + Ibrutinib 200 mg/kg | average | 0.0 | −1.8 | −3.8 | −3.3 | −3.0 | −4.3 |
| | SD | 0.0 | 0.7 | 0.9 | 2.6 | 1.2 | 3.2 |
| 8. Ibrutinib 100 mg/kg | average | 0.0 | −0.4 | −1.1 | −0.2 | 0.8 | −0.1 |
| | SD | 0.0 | 1.4 | 1.9 | 1.8 | 1.5 | 1.8 |
| 9. Ibrutinib 200 mg/kg | average | 0.0 | −1.5 | −1.2 | 0.2 | −0.4 | −1.6 |
| | SD | 0.0 | 2.4 | 1.9 | 1.3 | 1.3 | 1.5 |

The invention claimed is:

1. A medicament for cancer treatment comprising (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide or a pharmaceutically acceptable salt thereof and ibrutinib or a pharmaceutically acceptable salt thereof.

2. The medicament of claim 1, wherein the (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide or the pharmaceutically acceptable salt thereof and ibrutinib or the pharmaceutically acceptable salt thereof are separately contained in different formulations.

3. The medicament of claim 1, wherein the (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide or the pharmaceutically acceptable salt thereof and ibrutinib or the pharmaceutically acceptable salt thereof are contained in a single formulation.

4. A kit comprising the medicament of claim 1.

5. A method of treating a hematological malignancy comprising administering (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide or a pharmaceutically acceptable salt thereof and ibrutinib or a pharmaceutically acceptable salt thereof in combination.

6. The medicament of claim 1, wherein the salt of (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide is p-toluenesulfonate.

7. The method of claim 5, wherein the salt of (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide is p-toluenesulfonate.

8. The method of claim 5, wherein the hematological malignancy is chronic lymphatic leukemia (CLL), small lymphocytic lymphoma (SLL), high-risk CLL, non-CLL/SLL lymphoma, follicular lymphoma (FL), diffuse large B cell lymphoma (DLBCL), mantle cell lymphoma (MCL), Waldenstrom's macroglobulinemia, multiple myeloma (MM), marginal zone lymphoma, Burkitt's lymphoma, non-Burkitt high-grade B cell lymphoma, extranodal marginal zone B cell lymphoma, acute or chronic myelogenous (myelocytic) leukemia, myelodysplastic syndrome or acute lymphoblastic leukemia.

9. The method of claim 5, wherein the hematological malignancy is a hematological malignancy confirmed to be MDM2 inhibitor-sensitive using a gene signature.

10. The method of claim 5, wherein the (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide or the pharmaceutically acceptable salt thereof and the ibrutinib or the pharmaceutically acceptable salt thereof are administered in combination.

11. The method of claim 5, wherein the (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide or the pharmaceutically acceptable salt thereof and the ibrutinib or the pharmaceutically acceptable salt thereof are administered at the same time or different times.

12. A method of treating cancer comprising administering (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide or a pharmaceutically acceptable salt thereof and ibrutinib or a pharmaceutically acceptable salt thereof in combination, wherein the cancer is characterized by BTK activation.

13. The method of claim 12, wherein the cancer is a B cell tumor, mantle cell lymphoma (MCL), chronic lymphatic leukemia (CLL), diffuse large B cell lymphoma (DLBCL), or multiple myeloma (MM).

14. The method of claim 12, wherein the cancer is cancer confirmed to be MDM2 inhibitor-sensitive using a gene signature.

15. The method of claim 12, wherein the salt of (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide is p-toluenesulfonate.

16. The method of claim 12, wherein the (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide or the pharmaceutically acceptable salt thereof and the ibrutinib or the pharmaceutically acceptable salt thereof are administered in combination.

17. The method of claim 12, wherein the (3'R,4'S,5R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide or the pharmaceutically acceptable salt thereof and the ibrutinib or the pharmaceutically acceptable salt thereof are administered at the same time or different times.

* * * * *